(12) United States Patent
De Clercq et al.

(10) Patent No.: US 11,872,446 B2
(45) Date of Patent: Jan. 16, 2024

(54) LOW IMPACT RUNNING

(71) Applicant: UNIVERSITEIT GENT, Ghent (BE)

(72) Inventors: Dirk De Clercq, Sint-Niklaas (BE); Marc Leman, Zwevezele (BE); Joren Six, Gentbrugge (BE); Valerio Lorenzoni, Ghent (BE); Joeri Gerlo, Ghent (BE); Pieter Van Den Berghe, Ghent (BE)

(73) Assignee: UNIVERSITEIT GENT, Ghent (BE)

( * ) Notice: Subject to any disclaimer, the term of this patent is extended or adjusted under 35 U.S.C. 154(b) by 217 days.

(21) Appl. No.: 17/252,589

(22) PCT Filed: Jun. 25, 2019

(86) PCT No.: PCT/EP2019/066738
§ 371 (c)(1),
(2) Date: Dec. 15, 2020

(87) PCT Pub. No.: WO2020/002275
PCT Pub. Date: Jan. 2, 2020

(65) Prior Publication Data
US 2021/0252338 A1 Aug. 19, 2021

(30) Foreign Application Priority Data
Jun. 28, 2018 (EP) .................................... 18180427

(51) Int. Cl.
*A63B 24/00* (2006.01)
*G16H 20/30* (2018.01)

(52) U.S. Cl.
CPC ......... *A63B 24/0062* (2013.01); *G16H 20/30* (2018.01); *A63B 2024/0078* (2013.01);
(Continued)

(58) Field of Classification Search
CPC ........ A63B 24/0062; A63B 2024/0078; A63B 2220/17; A63B 2220/30; A63B 2220/53; A63B 2225/50; G16H 20/30
See application file for complete search history.

(56) References Cited

U.S. PATENT DOCUMENTS 10,152,898 B2 * 12/2018 Rhea ........................ G09B 5/02
11,464,209 B2 * 10/2022 Ishikawa ................ G16H 20/30
(Continued)

FOREIGN PATENT DOCUMENTS

WO 2015164456 A2 10/2015

OTHER PUBLICATIONS

Clansey et al., "Influence of Tibial Shock Feedback Training on Impact Loading and Running Economy," Medicine & Science in Sports & Exercise, Official Journal of the American College of Sports Medicine, vol. 46, No. 5, Sep. 30, 2013, pp. 973-981.
(Continued)

*Primary Examiner* — Malina D. Blaise
(74) *Attorney, Agent, or Firm* — Workman Nydegger

(57) ABSTRACT

A method for gait retraining of a runner includes: measuring acceleration data of at least one lower leg of the runner; diagnosing the acceleration data thereby determining a measure of the impact intensity of at least one external tibial shock; and providing real-time feedback to the runner by converting the measure of the impact intensity into distortion of music to a level which is perceived by the runner as a measure for the impact intensity. The conversion is done based on a predefined relationship between perceived distortion levels and imposed distortion levels, and the runner can reduce the distortion of the music by adjusting his or her gait.

15 Claims, 6 Drawing Sheets

(52) U.S. Cl.
CPC ....... *A63B 2220/17* (2013.01); *A63B 2220/30* (2013.01); *A63B 2220/53* (2013.01); *A63B 2225/50* (2013.01)

(56) References Cited

U.S. PATENT DOCUMENTS

| | | | | |
|---|---|---|---|---|
| 11,465,030 | B2* | 10/2022 | Putnam | G06Q 50/01 |
| 11,468,711 | B2* | 10/2022 | Hoffman | A61B 5/1118 |
| 11,468,977 | B2* | 10/2022 | Roy | A61B 5/1114 |
| 2011/0046687 | A1* | 2/2011 | Naschberger | A61H 23/0236 |
| | | | | 607/3 |
| 2019/0099134 | A1* | 4/2019 | Bennett | G06N 20/00 |
| 2021/0169417 | A1* | 6/2021 | Burton | A61B 5/4857 |
| 2022/0319654 | A1* | 10/2022 | Parvaneh | G16H 20/30 |

OTHER PUBLICATIONS

Wood et al., "Use of Audio Biofeedback to Reduce Tibial Impact Accelerations During Running," Journal of Biomechanics, vol. 47, No. 1, Mar. 3, 2014, pp. 1739-1741.

Hunt et al., "The Influence of Auditory-Motor Coupling on Fractal Dynamics in Human Gait," Scientific Reports, vol. 4, Issue 5879, Aug. 1, 2014, pp. 1-6.

Giandolini et al., "Foot Strike Pattern and Impact Continuous Measurements During a Trail Running Race: Proof of Concept in a World-Class Athlete," Footwear Science, Mar. 4, 2015, pp. 1-11.

Tate et al., "Sound-Intensity Feedback During Running Reduces Loading Rates and Impact Peak," Journal of Orthopaedic & Sports Physical Therapy, vol. 47, No. 8, Aug. 1, 2017, pp. 565-569.

Van Den Berghe et al., "Real-Time Music-Based Biofeedback to Reduce Impact Loading During Over-Ground Running," 42nd Annual Meeting of the American Society of Biomechanics, Aug. 8-11, 2018, 2 Pages.

Lorenzoni et al., "A Biofeedback Music-Sonification System for Gait Retraining," Movement and Computing, ACM, Jun. 28-30, 2018, 5 Pages.

Extended European Search Report and Written Opinion from corresponding Application No. EP18180427.0, dated Dec. 7, 2018.

International Search Report and Written Opinion from PCT Application No. PCT/EP2019/066738, dated Sep. 3, 2019.

* cited by examiner

LOW IMPACT RUNNING

FIELD OF THE INVENTION

The invention relates to the field of gait retraining. More specifically it relates to methods and systems which support a runner in gait retraining.

BACKGROUND OF THE INVENTION

Gait retraining of a runner has the advantage that it has the potential to manage and decrease running related injuries of the runner. This is especially important for high impact runners, defined as runners with elevated impact intensity compared to their peers.

The use of biofeedback in current gait retraining methods nowadays primarily relies on computer screens to show visual information of biomechanical data. Arguably, this set-up presents limitations in terms of portability and limits attention.

Wood and Kipp showed the potential of using audio feedback to influence runner's performances compared to visual feedback (Claire M Wood and Kristof Kipp. 2014. Use of audio biofeedback to reduce tibial impact accelerations during running. Journal of biomechanics 47, 7 (2014), 1739-1741). In the laboratory setup disclosed in Wood a beep is generated when a threshold is crossed. A foot strike with a greater PPA will result in a beep with a higher pitch.

In such systems the measure of impact intensity may for example be obtained using an accelerometer. For continuous registration of 3D tibial accelerometry, wireless accelerometer units have been used (e.g. Hikob Agile Fox by Giandolini et al., 2015, Foot strike pattern and impact continuous measurements during a trail running race).

WO2015/164456 A2 relates to gait retraining. It discloses a system which allows quantitative analysis of a subject's gait. Feedback is realized by generating different sounds/vibrations as the subject's gait pattern changes, or as the intensity of the impact with the ground varies. Biofeedback on impact intensity has already been described in laboratory set up, but never in real-time running environment because this necessitates a fully wearable system that accounts for the natural variation in real running environment. Bound to a treadmill/lab environment, research groups have provided audio and/or visual biofeedback on tibial impact shock (Cheung 2017, Clansey et al. 2014, Crowell et al. 2010-2011, Wood & Kipp 2014).

There is therefore a need for biofeedback systems which are fully wearable and therefore operable in a natural running environment and which provide good feedback to the runner which allows him to retrain his gait, preferably at an instructed or preferred running speed.

SUMMARY OF THE INVENTION

It is an object of embodiments of the present invention to provide systems and methods which support a runner in gait retraining.

In a first aspect embodiments of the present invention relate to a method for gait retraining of a runner. The method comprises:
measuring acceleration data of at least one lower leg of the runner,
diagnosing the acceleration data thereby determining a measure of the impact intensity of at least one external tibial shock,
and providing real-time feedback to the runner by converting the measure of the impact intensity into distortion of music that is perceptible by the runner, wherein the conversion is done based on a predefined relationship between perceived distortion levels and imposed distortion levels.

Based on the real-time feedback the runner can adjust the gait and hence also the accelerations of the at least one leg and as a result the runner can adjust the acceleration data that is measured. By adjusting the gait, the runner can therefore reduce the distortion of the music such that an increased (e.g. maximum) musical clarity (i.e. music with reduced noise distortion) is obtained. The relationship between the distortion of the music and the impact intensity is defined by a predefined relationship between the perceived distortion level and the imposed level of distortion. The predefined relationship may be experimentally determined.

This method would not be effective if this predefined relationship would not be considered because without this information the runner would not be able to effectively adjust the gait to reduce the distortion of the music. It is therefore advantageous that a method, according to embodiments of the present invention distorts the music to a level which is perceived as a measure for the impact intensity of at least one tibial shock. In embodiments of the present invention the distortion of the music is noise-based distortion.

It is an advantage of embodiments of the present invention that they provide real-time feedback that enables the runner to make adjustments to the running technique to reduce cumulative musculoskeletal loading for a given running speed. Thus, a reduced impact loading at the lower extremity can be achieved through gait retraining to manage and potentially prevent running-related injuries.

Methods according to embodiments of the present invention may comprise measuring the running speed and providing real-time feedback to the user about the running speed.

The real-time feedback about the speed allows the runner to adjust its speed such that a constant speed is achieved. The resulting speed may for example be constant within +/−5% of a pre-chosen target speed (m/s). This is advantageous for gait retraining because the gait retraining is more effective when running at a constant speed.

In embodiments of the present invention the real-time feedback is only provided if the measure of the impact intensity is crossing a predefined threshold.

It is an advantage of embodiments of the present invention that the music is only distorted if a predefined threshold is crossed. This allows the runner to run without distorted music as long as the measure of the impact intensity does not cross a predefined threshold. Only if the predefined threshold is crossed, the user will perceive distorted music. The predefined threshold may for example by default be determined based on a large database acquired during profound testing of a large representative sample of runners (database default settings). The threshold may be modifiable by the end-user or gait-retraining expert. The predefined threshold may be speed dependent.

In embodiments of the present invention distortion of music is achieved by adding white noise, or by adding pink noise, or by adding amplitude modulated noise to the music, or by downsampling the music, or by decreasing the volume of the music.

In embodiments of the present invention the distortion of music is changed in steps of discrete pre-defined levels.

It is an advantage of embodiments of the present invention that by changing the intensity level of the distortion in discrete steps, the probability of detecting a change in the distortion can be increased. The discrete pre-defined levels may for example be selected such that a one-step change of the distortion is detectable by the user. The may be obtained by experimental verification.

In embodiments of the present invention the tempo of the music is adjusted to the tempo of the running cadence. This adjustment may for example be done if a ratio of steps per minute versus beats per minute of the song does not fall within predetermined boundaries during a certain period. Changing the beats per minute of the song may be achieved by real-time stretching of audio and if necessary by changing the speed of the song or by playing another song. The goal of this synchronization is to align the musical tempo with that of the gait tempo so that a rewarding coupling between movement and music can be experienced when no noise is added.

In embodiments of the present invention the method comprises providing a plurality of gait retraining sessions wherein each session comprises the measuring, diagnosing and providing real-time feedback during a certain period of time and wherein at least for one subsequent session compared to a previous session the distortion of music for a certain measure of impact intensity has a smaller duration and/or level for the subsequent session, thus obtaining fading of the feedback from the previous session to the subsequent session.

It is an advantage of embodiments of the present invention that the method can be adjusted such that it facilitates reinforced motor learning based on principles of 'reward' and 'punishment'. 'Reward' can occur when music gets nicely aligned to gait, and/or when noise distortion is less intense or disappears due to low impact shocks. In contrast, 'punishment' can occur when noise distortion in addition to music gets more and more intense due to high impact shocks.

In embodiments of the present invention the infading or outfading of the feedback noise is dynamic and depends on the measured acceleration data of previous sessions. It is thereby an advantage that the in/outfading of the feedback is dynamic and depends on how good the runner reacts to the biofeedback.

In embodiments of the present invention diagnosing the acceleration data comprises applying a peak detection algorithm for obtaining the measure of the impact intensity.

The maximum value of the acceleration data within the first 50 ms after foot contact with the ground may for example be used as a measure of the impact intensity. Also, other values which are caused by the external tibial shock may be derived from the acceleration data, as long as they are a measure of the impact intensity of at least one tibial shock. The magnitude of the impact intensity may also be obtained by averaging the acceleration data over a plurality of foot contacts. Other possible measures for the impact intensity may be obtained from the frequency content, and from the rate of change of the measured accelerations.

In embodiments of the present invention the peak detection algorithm comprises determining a maximum value of the acceleration data within the first 50 ms after foot contact.

In embodiments of the present invention the peak detection algorithm comprises determining a size of a 1D-component of the acceleration data for obtaining the measure of the impact intensity.

If the acceleration is measured in only one dimension the measured data corresponds with the size of the 1D-component. The direction of the 1D-component may for example be parallel with the axial direction of the tibia. If the acceleration is measured in three dimensions the size of a 1D-component of each separate acceleration vector may be determined. The vector sum of the three separate 1D-components corresponds with the norm of the acceleration data and may be used as measure of the impact intensity.

In embodiments of the present invention the peak detection algorithm comprises finding a peak of which the size of the 1D component is larger than a peak detection threshold (C), and finding this peak within an expected time window wherein the size (D) of the time window is dependent on the expected pace period.

It is an advantage of embodiments of the present invention that the peak detection is done within an expected time window wherein the peak should occur. By selecting the size of the time window properly it can be avoided that two peaks are detected within one time window.

The peak detection threshold C and the time interval D may be pre-defined, or they may be dynamically adapted while running. The expected pace period may be retrieved by statistical analysis on a database of different runner profiles and/or based on a measured pace period while running.

In a second aspect embodiments of the present invention relate to a biofeedback system for gait retraining of a runner. The biofeedback system comprises:
at least one sensor mountable against the lower leg of the runner and adapted to measure acceleration data along at least one axis,
a processing unit adapted for diagnosing the acceleration data thereby determining a measure of the impact intensity of at least one external tibial shock,
an interface unit adapted for providing real-time feedback to the runner by converting the measure of the impact intensity into distortion of music that is perceptible by the runner, wherein the conversion is done based on a predefined relationship between perceived distortion levels and imposed distortion levels.

In embodiments of the present invention the sensor is an accelerometer or an inertial measurement unit. The interface unit is providing the real-time feedback to the runner by converting the measure of the impact intensity into distortion of music and by passing the distorted music to the runner.

Biofeedback systems according to embodiments of the present invention are designed in a way to minimally disturb the natural movement of the runner (e.g. mounting of the accelerometer on the lower leg, with a comprehensive strapping module, that combines user comfort and high frequency response).

Biofeedback systems according to embodiments of the present invention are designed in a way to have a high frequency response that allows measuring external tibial accelerations in a reliable way.

In embodiments of the present invention the sensor is adapted for wirelessly transmitting the acceleration data to the processing unit.

In embodiments of the present invention the biofeedback system moreover comprises a speed sensor, or is adapted for interfacing with a speed sensor for measuring a speed of the runner and the processing unit is adapted for diagnosing the acceleration data in function of the measured speed and/or the interface unit is adapted for providing real-time feedback of the measured speed.

It is an advantage of embodiments of the present invention that also the pace of running and hence the speed of the runner can be adjusted by real-time feedback of the measured speed.

In embodiments of the present invention the biofeedback system is adapted for storing the measured acceleration data and/or the measures of the impact intensity and/or the measured speed.

It is an advantage of embodiments of the present invention that the stored data can be used for post-hoc analysis.

In embodiments of the present invention the biofeedback system is comprising a communication unit adapted to synchronize data with at least one external measurement system.

Such an external measurement system may for example be a motion capture system.

In embodiments of the present invention gait retraining is achieved by addressing auditory-motor couplings that can be influenced through a real-time ongoing auditory stimulus (made of music and added noise distortion) that provide continuous feedback to the motor activity. This type of auditory stimulus is called "embodied" because it is tightly connected to body movement, and to the associated reinforcement learning (based on 'reward' when distortion of music disappears and music is nicely synchronized with the running, and 'punishment' when music gets distorted due to high impact running). The "embodied" stimulus stands in sharp contrast to auditory stimuli that operate as a "signal" (e.g. pitch of a warning tone) of a measure that surpasses a threshold. The embodied auditory stimuli objective is accomplished by a method and device according to embodiments of the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 3, including

FIG. 9, including

Figure 1:
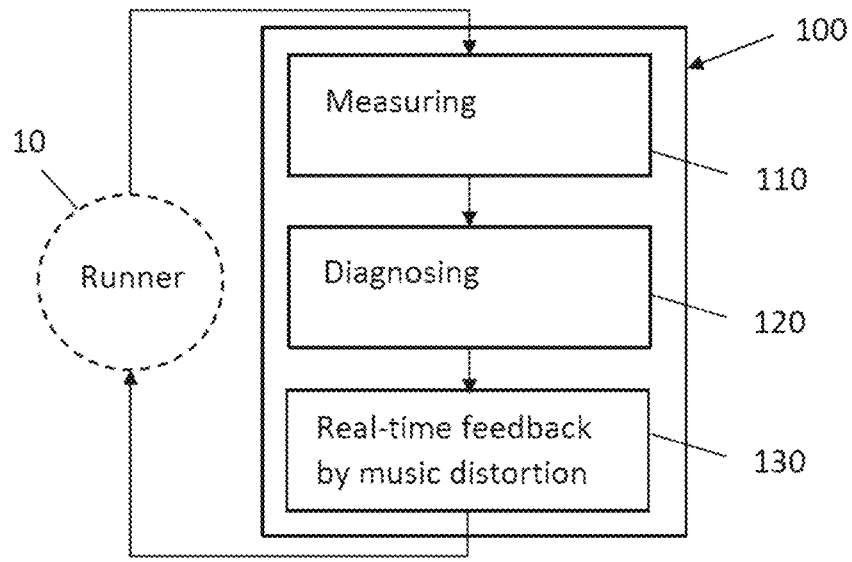
FIG. 1 shows a flow chart of a method in accordance with embodiments of the present invention.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings, but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to real-time feedback, real-time refers to the fact that the feedback is given within a period which allows the runner to close the feedback loop and perceive the magnitude of impact intensity with or without a change in the distortion levels because of his or her change(s) in running gait.

In a first aspect embodiments of the present invention relate to a method 100 for gait retraining of a runner 10. The method comprises measuring 110 acceleration data of at least one lower leg of the runner. The method moreover comprises diagnosing 120 the acceleration data thereby determining a measure of the impact intensity of at least one external tibial shock in at least one dimension and providing 130 real-time feedback to the runner by converting the measure of the impact intensity into distortion of music that is perceptible by the runner, wherein the conversion is done based on a predefined relationship between perceived distortion levels and imposed distortion levels.

A flow chart comprising method steps in accordance with embodiments of the present invention is illustrated in FIG. 1. The user 10 in this method closes the feedback loop. By providing real-time feedback about the acceleration data the user can adjust his or her running technique based on this feedback such that the music becomes less distorted. It is thereby important that the perceived distortion level is a good measure for the impact intensity as this allows the user to better adjust his gait. In methods according to embodiments of the present invention the impact shock is mapped to the distortion level played on top of the music and the reward consists in minimization or removal of noise, i.e. improvement of the music quality. In embodiments of the present invention the music is synchronized to the runner's cadence.

The method works optimal if the runner is running at a constant speed (m/s) (e.g. within a margin of +/−20%, or even better +/−10%, or even better within a margin of +/−5%. The runner may run in a natural running environment. The method may even comprise a step measuring the running speed and providing feedback to the runner such that he can maintain a constant running speed.

In a second aspect embodiments of the present invention relate to a biofeedback system 200.

The biofeedback system preferably is a wearable system. It is for example applicable for impact sonification applications in overground settings. In embodiments of the present invention the biofeedback system can continuously measure 1D or even 3D tibial accelerations with an embedded algorithm to detect tibial impact shock in real-time for music-based impact sonification.

Figure 2:
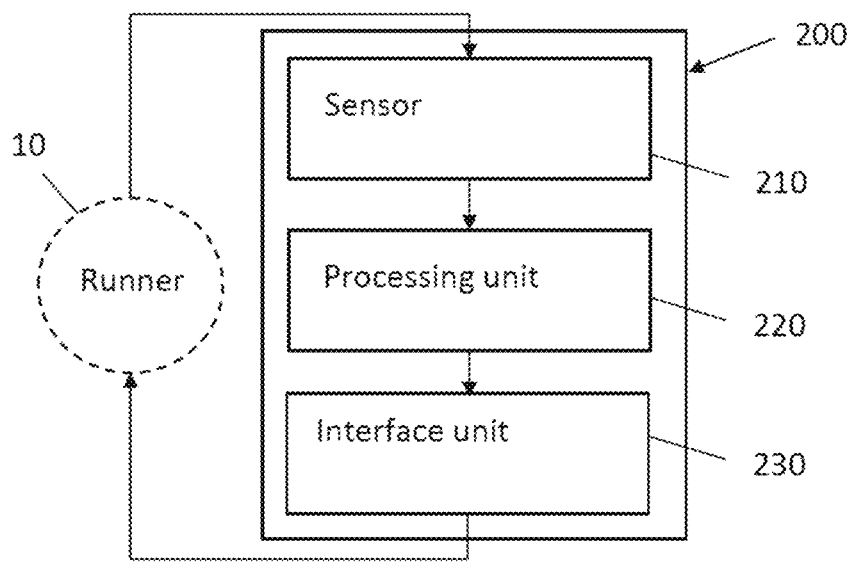
FIG. 2 shows a schematic drawing of a biofeedback system in accordance with embodiments of the present invention.

The biofeedback system comprises a sensor 210 which is adapted for monitoring external impact shocks experienced by the lower limb during locomotion. These repetitive external impact shocks can be considered as a proxy for the cumulative loading of the musculoskeletal system, especially of the bones in the lower leg (e.g. tibial bone). The biofeedback system comprises a processing unit 220 for diagnosing the acceleration data (e.g. for peak detection) and an interface unit 230 for impact sonification. An example of such a biofeedback system is schematically illustrated in FIG. 2.

The sensor may be adapted for generating tibial-worn acceleration data in at least one axis and for registering the acceleration data. The measurements may be done over a set time period during the physical activity.

The sensor may be an accelerometer or an inertial measurement unit (IMU) and may comprise a housing within which the sensor is mounted.

The accelerometer may be configured to measure acceleration with respect to at least one local axis. It may support two or multiple-axes. In an exemplary embodiment of the present invention the motion sensor supports three-dimensional measurements.

In embodiments of the present invention the sensor may comprise a transmitter module for transmitting the acceleration data to the processing unit either directly, or via an intermediate receiver module linked to the processing unit. This communication may be wireless.

Sensors 210 according to embodiments of the present invention may be mounted against each lower leg. Mounting of the sensors may for example be done as follows: the tibial skin may be bilaterally pre-stretched before the accelerometers are attached over the distal, anteromedial aspect of both tibia. These sensors are connected with the processing unit thus allowing automatized determination of the average tibial loading of both legs.

The at least one sensor 210 which is used for measuring the tibial impact shock may for example be a lightweight tri-axial accelerometer. The weight may for example be below 50 mg, or even below 30 mg, for example 20 mg. An example of such an accelerometer is the LIS331, Sparfkun, Colo., USA; which has a sampling frequency of 1000 Hz and a weight of 20 mgram. In an exemplary embodiment of the present invention the accelerometer is fitted in a shrink socket (which may for example have a total mass<3 gram).

The sensor may be a low-power MEMS tri-axis accelerometer with digital output (SPI-compatible) and an accuracy of 70 mg, supporting a range of ±24 g and a sampling rate of 1000 Hz (STMicroelecronics, 2011).

The processing unit 220 is adapted for diagnosing the acceleration data thereby determining a measure of the impact intensity of at least one external tibial shock.

It may for example be configured for receiving the acceleration data and for determining the peak tibial acceleration for each approximated foot strike. It may be configured to calculate and determine one or more variables from the incoming acceleration data. For each footfall, the peak tibial acceleration of the axial (1D) or resultant (3D) component may for example be determined.

Figure 3A:
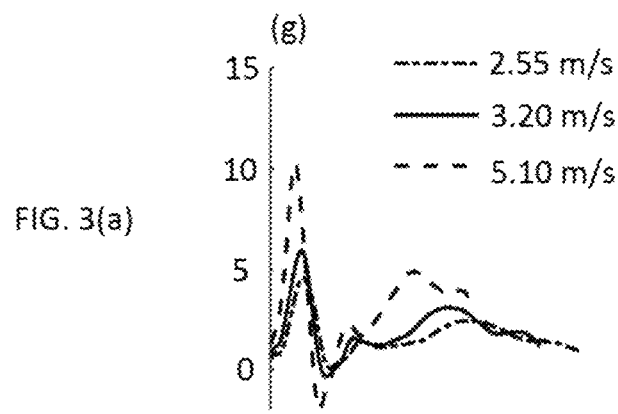
FIGS. 3(a) to 3(c), show tibial accelerations obtained using a biofeedback system in accordance with embodiments of the present invention.
Figure 3B:
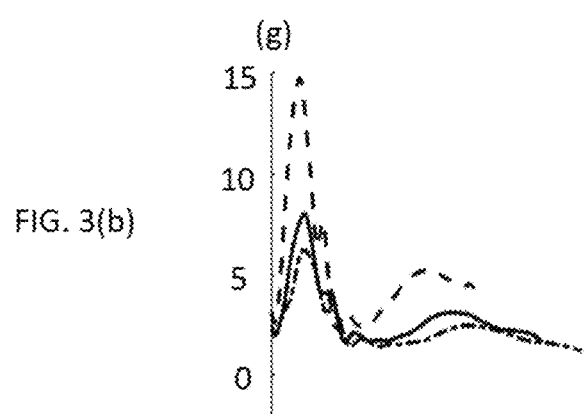
Figure 3C:
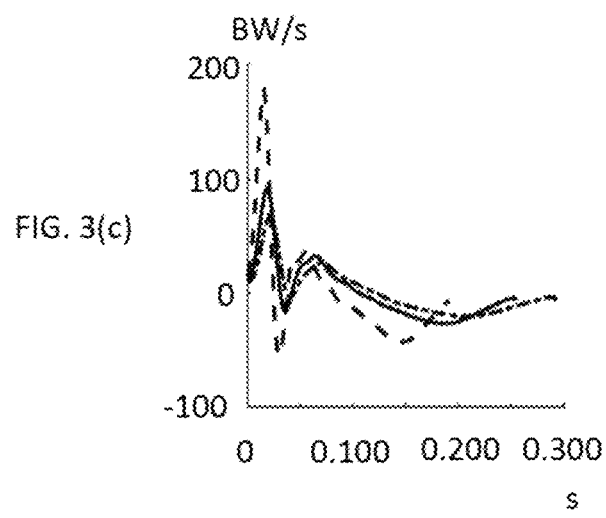

An example of mean time series (expressed in s) of tibial accelerations in the axial (a, expressed in units of g) and resultant (b, expressed in units of g) dimensions and synchronized to the vertical loading rate of the ground reaction force during stance (c, expressed in BW/s, wherein BW is body weight) are illustrated in FIG. 3. Stance was interpolated to mean contact time. The accelerations are shown for different running speeds: 2.55 m/s, 3.2 m/s, and 5.1 m/s.

It is found by the inventors that the peak tibial acceleration (PTA) is a valid measurement of impact intensity that is reliable within, plus repeatable between sessions. The results of FIG. 3 where obtained using a biofeedback system in accordance with embodiments of the present invention, which was able to continuously measure three-dimensional tibial accelerations, with an embedded algorithm to detect tibial shock in real-time. Using this system the measurement agreement between PTAs and Loading Rates (LR) during overground running was assessed.

In embodiments of the present invention the processing unit 220 may be a micro-controller or any other controller or processor such as for example a processor embedded in a smart phone.

In embodiments of the present invention the processing unit is adapted for collecting data from the sensor 210. This may be through a wireless connection with the sensor.

In an exemplary embodiment of the present invention the processing unit comprises a Teensy 3.2 micro-controller and a tablet. The micro-controller is connected via USB to the 7" tablet (Panasonic Roughpad FZ-M1) mounted on a stripped backpack. In this example the weight of the backpack is 1.6 kg. For the experiment it was properly attached to the back so that it did not feel as disturbing the natural running movement. In this exemplary embodiment of the present invention the processing unit is a tablet, however, processing may for example also be done on a smartphone, smartwatch, mobile central unit, or even cloud based.

A biofeedback system 200 according to embodiments of the present invention comprises an interface unit 230 which is adapted for providing real-time feedback to the runner by converting the measure of the impact intensity into distortion of music that is perceptible by the runner, wherein the conversion is done based on a predefined relationship between perceived distortion levels and imposed distortion levels. Throughout the description this concept is also referred to as impact sonification with mapping. The impact sonification provides real-time feedback of the performance through introduction of distortion of a baseline music track.

The interface unit 230 may be a wearable or ambulant device connected to the microprocessor that generates real-time music-based biofeedback and additionally also may be configured to provide audible and/or visual feedback on the running speed.

In embodiments of the present invention the music-based continuous feedback may thereby consist of pink noise with a predefined (e.g. exponential) mapping added to music. Musical stimuli have the advantage that they may be very motivating and have an effect on the strength or vigor of the movement. It is moreover advantageous that the tibial impact shock is used as mobile feedback variable as this variable relates to running related injuries (e.g. tibial stress fracture). It is an advantage of embodiments of the present invention that the impact severity is significantly reduced by introducing the music-based continuous feedback of the impact intensity of the at least one tibial shock. Based on this feedback the runners adapt their gait leading to more sustainable neuromuscular/motor learning adaptations. These learning adaptations are more effective in long term changes in running style.

In embodiments of the present invention the feedback on the impact intensity may be combined with feedback on the running speed and the possibility to synchronize to other measurement equipment if required. The beats per minute of the music can be continuously matched to the runners' steps per minute.

The interface unit 230 comprises a headphone or earbuds for passing the augmented feedback to the user.

In the exemplary embodiment of the present invention the interface unit is implemented in a specifically designed Max/MSP patch running on the tablet and played by the same tablet through Sennheiser headphones. The invention is, however, not limited thereto.

The music may for example be downloaded on the biofeedback system or it may be available through streaming.

Data transmission may be achieved via the Open Sound Control message protocol and/or via a wireless network.

In embodiments of the present invention the measure of the impact intensity of at least one external tibial shock is determined in real-time while running. This may for example be achieved by peak detection to detect a tibial impact shock for sensor signals of the left and right lower leg.

In an exemplary embodiment of the present invention the value of the acceleration in the axial dimension of the lower leg is compared with a threshold. If the value in the axial dimension is above the threshold (e.g. 3.5 g) and no larger value appears in the next period of time which may for example be 0.375 s, then a footfall happened. For determining the peaks associated with a footfall, a pre-determined waiting period between peaks may be used. A more detailed explanation of a possible peak detection algorithm is described at the end of the description.

In an exemplary embodiment of the present invention the processing unit processes the acceleration data in real-time. Thereby steps are detected, and cadence is calculated.

A biofeedback system according to embodiments of the present invention may be calibrated in the laboratory by comparison of tibial impact shock with gold standard measure of impact severity, namely the peak loading rate of the ground reaction force by means of immobile force plates.

In some embodiments of the present invention the real-time feedback is only provided if the measure of the impact intensity is crossing a predefined threshold. This threshold may be obtained by risk assessment of impact related injuries when running steady-state, over-ground, level at a common training speed. In embodiments of the present invention the target for impact reductions may be chosen by the runners or their medical team. This may be done in function of the risk assessment. In order to set valid thresholds for the at-risk impact shock level, and valid levels for the impact reduction, actual individual measures may be combined with a criteria-algorithm based on a vast reference data base.

The predefined threshold may be crossed by exceeding it. A sonic feedback signal is generated for gait retraining of a runner to reduce the impact when running. In that case the goal is to reduce overuse injuries by reducing the impact shocks.

In some embodiments the predefined threshold may be exceeded by going below the threshold. Also, here a sonic feedback signal may be provided, however, in this case for gait retraining of a runner to increase the impact when running. This may be applied as a bone strengthening training (e.g. to prevent osteoporosis). The system may therefore be configured with the aim to reach a certain daily bone load in size (e.g. in peak tibial acceleration) and/or in frequency.

In embodiments of the present invention the biofeedback system comprises a communication unit which is adapted to synchronize data with at least one external measurement system. When the external measurement system is a motion capture system this allows accurate synchronization of accelerations to the (passive) motion capture system.

The biofeedback system may operate stand-alone but, in embodiments of the present invention, it may be connectable with other measurement equipment and able to operate complementary with the other measurement equipment.

The biofeedback system may for example comprise an infrared sensor. It may for example be configured to synchronize tibial accelerations with infrared light of an external source up to millisecond precision (e.g. when the biofeedback system is functioning as measurement system). Whereas wireless inertial measurement units are inherent to delay and transmission variability, in embodiments of the present invention a separate infrared sensor may be present which is configured to capture, simultaneously with the accelerations, infrared signals from infrared cameras of any passive motion capture system.

In embodiments of the present invention the biofeedback system may be adapted for controlling the speed of the runner by sonic feedback (e.g. by telling slower or faster or any other sonic feedback). The biofeedback system may be adapted for diagnosing the acceleration data in function of the measured speed.

The biofeedback system may be configured to communicate with a speed monitoring system for obtaining the speed of the runner. This may for example be an indoor speed monitoring system (e.g. a calibrated beacon system). Alternatively, the biofeedback system may comprise a GPS to receive a periodic indication of the speed of the runner. Such a GPS system is for example applicable in an overground outdoor environment.

In the context of gait retraining, it is preferable that the impact severity is reduced by gait alteration instead of by reducing the running speed. The impact severity is namely directly linked to running speed. The running speed should therefore preferably be kept as constant as possible.

In embodiments of the present invention the biofeedback system does not interfere with step frequency as the tempo of the music adapts based on the step frequency (steps per minute=beats per minute).

The processing unit 220 and the interface unit 230 may be implemented by providing an application on a mobile device. The mobile device may thereby be connected to a wireless sensor. When the application is running on the mobile device it logs parameters derived from tibial accelerometry and is able to provide real-time music-based biofeedback on tibial impact shock.

In embodiments of the present invention the processing unit 220 and the interface unit 230 are comprising a computer-readable medium having stored thereon computer executable instructions that, when executed on the processing unit and the interface unit, cause the processing unit and the interface unit to determine a measure of the impact intensity of at least one external tibial shock, and to provide feedback to the runner by converting the measure of the impact intensity into distortion of music that is perceptible by the runner. This feedback may be real-time feedback.

The computer executable instructions may for example be written in Java.

The processing unit and the interface unit may be configured such that it complies with one or more of the following features:
diagnosis of the acceleration data comprises distinguishing cyclic movement patterns (e.g. walking, running) because of the repeated foot-ground contacts when physically active;
real-time biofeedback of the running gait comprises a real-time and continuous transfer of motion parameters (such as cadence and impact shock) into sound and music;
musical parameters (tempo and pitch) are aligned with a motion parameter (cadence) through real-time time stretching of the music;
the personalized biofeedback data may identify the movement pattern having the lowest peak accelerations for each runner;
the acceleration data of a gait retraining session is compared to the calculated average axial or resultant peak acceleration magnitude associated with the last 5 strides.
a real-time alert sound is generated if any shock or speed variables exceed a predetermined threshold;
one or more gait retraining sessions of the runner are stored or are transmitted to the cloud for more advanced post-hoc analysis.

The acceleration data represents a series of discrete tibial shockwaves from the discrete footstrikes.

For consistency of the measurements the runner may be advised to wear similar footwear in each separate gait retraining session and to run at a constant speed. Methods and/or devices according to embodiments of the present invention may even be adapted for giving the runner sonic feedback in order to maintain this constant speed.

Methods and/or devices according to embodiments of the present invention may be applied to recreational as well as professional athletes. They can use the biofeedback system during training as well as during rehabilitation.

In embodiments of the present invention the measure of the impact intensity is converted into distortion of music that is perceptible by the runner. The conversion is done based on a predefined relationship between perceived distortion levels and imposed distortion levels. Thereby different sound types may be continuously added to the music instead of adding discontinuous beeps to the music.

Examples of sound types are white noise, pink noise, amplitude modulated noise, downsampling, and volume decrease.

Figure 4:
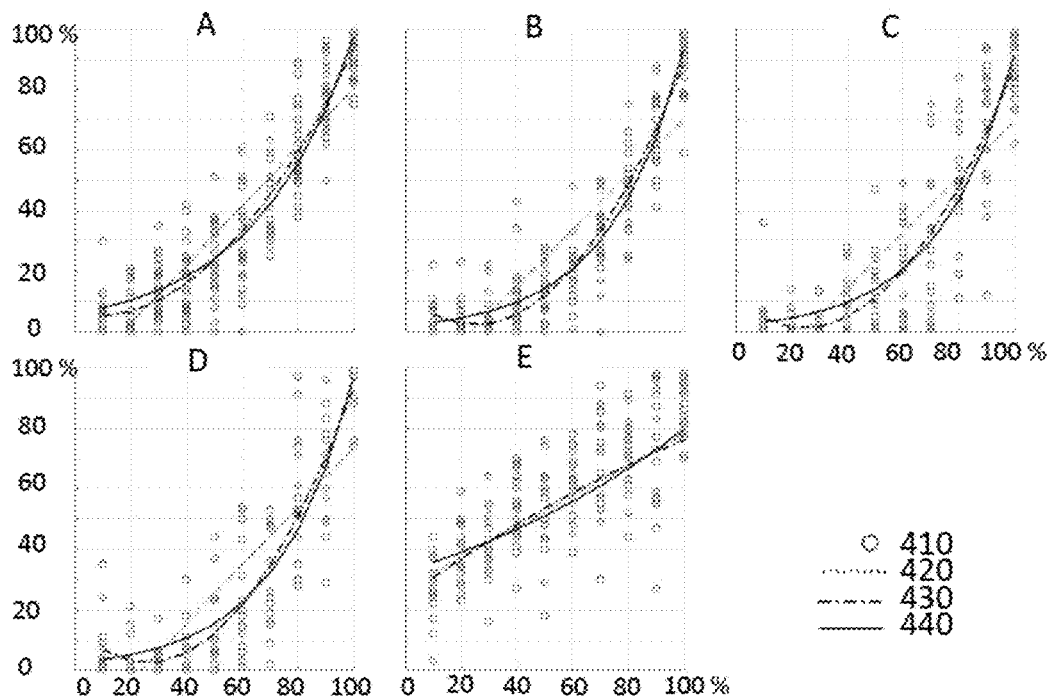
FIG. 4 shows experimentally determined relationships between perceived distortion levels and imposed distortion levels for different types of distortions in accordance with embodiments of the present invention.

In embodiments of the present invention the relationship between the perceived distortion levels and the imposed distortion levels may be experimentally determined. Examples thereof are shown in FIG. 4 for white noise (A), for pink noise (B), for amplitude modulated noise (C), for down sampling (D), and for volume decrease (E). For each of these graphs the horizontal axis shows the imposed level in % music rms and the vertical axis shows the perceived level in % music rms. The loudness level expressed as % music rms thereby refers to the percentage of the root mean square of the distorting signal with the distortion and music signals normalized for equal loudness (same root mean square value). In each graph the raw data 410, the linear fit 420, the $2^{nd}$ order fit 430 and the exponential fit 440 are shown.

An increased accuracy of the mapping between the perceived distortion levels and the imposed distortion levels results in an improved feedback stimulus to the runner (i.e. the runner will have a more accurate idea about the measure of the impact intensity of the external tibial shock). Typically, this relationship between the perceived distortion levels and the imposed distortion levels is a non-linear relationship.

In the case of pink noise, it was found that the exponential fit minimizes the integral: $I=\int_0^{100} f^{-1}(y) * \sigma(y) \, dy$, where $f^{-1}(y)$ indicates the inverse of the 0 interpolation function and $\sigma(y)$ the estimated standard deviation.

Pink noise with an exponential fit generated the most perceivable sonification. The signal consisting of pink noise superimposed on the music scored relatively well in terms of clarity and is therefore a good choice for gait retraining in accordance with embodiments of the present invention. It has moreover the additional advantage that it was considered as pleasant by the runner.

In an exemplary embodiment of the present invention the following relationship between the perceived distortion levels and the imposed distortion levels may be used in case of pink noise:

$$\text{output}=f.a*\exp(f.b.*\text{input})$$

with:
  f.a=5.9292
and:
  f.b=0.0279

In embodiments of the present invention the distortion of the music is changed in steps of discrete pre-defined levels. These levels may be experimentally verified. They may for example be selected such that an increase or decrease of one discrete level corresponds with a just noticeable difference between the intensity levels of the distortion. Through experiments the discrete pre-defined levels can be verified.

Figure 5:
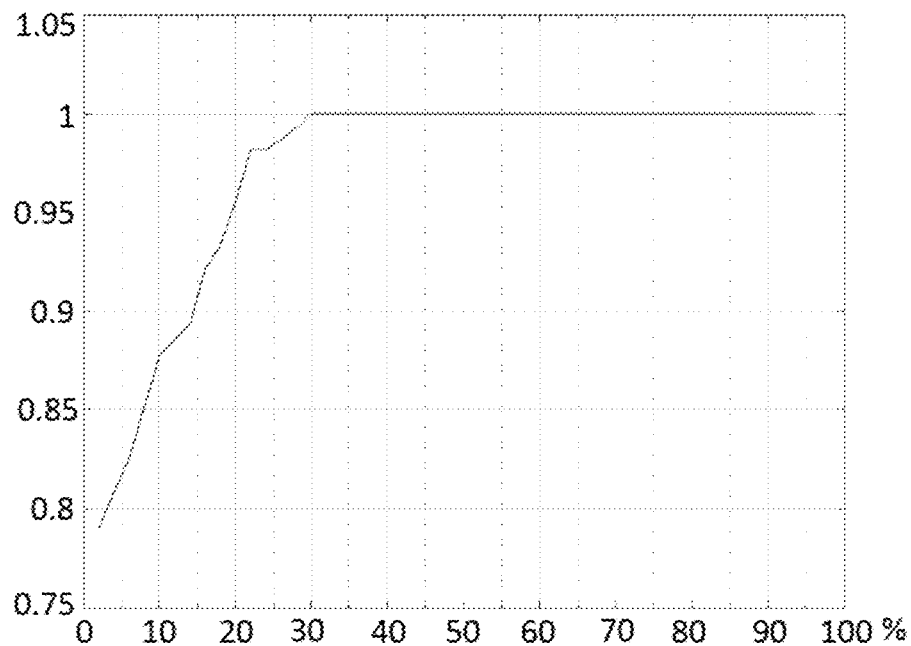
FIG. 5 shows the ratio of the detected discrete steps between distortion levels divided by the total number of steps for a certain interval size between the distortion levels in accordance with embodiments of the present invention.

FIG. 5 shows the ratio of the detected steps divided by the total number of steps for a certain interval size. The interval size is expressed in %. The noise intensity may for example be changed in discrete steps of about 20 on a scale of 0 to 100 for pink noise. It can be seen from this graph that this corresponds with a probability of 95% of detecting a change in the noise.

In embodiments of the present invention the discrete pre-defined levels may be configurable. Different measures of the impact intensities may be mapped on a different distortion intensity. In the example of pink noise illustrated in FIG. 5 a value of 20 for the step size provides a reasonably high probability of detection and leaves a margin for discretization into multiple categorical levels of distortion intensity. The number of discrete pre-defined levels may be selected such that also PTAs of high impact runners can be mapped on the pre-defined levels.

Diagnosing the acceleration data may comprise continuous registration of the acceleration data, determining a measure of the impact intensity (e.g. cyclic detection of the PTA, PTA's magnitude and timing), and providing this information in real-time to the interface unit.

The interface unit 230 converts the measure of the impact intensity into distortion based on the predefined relationship between perceived distortion levels and imposed distortion levels. For the measure of impact intensity, it may for example use a moving average of 5 PTA values. As discussed before the distortion may be pink noise which is scaled according to the measure of impact intensity according to the previously discussed predefined relationship.

Also, timing information may be provided to the interface unit to obtain a music-to-movement alignment. The interface unit is in that case configured to align the beats per minute of the music with the derived steps per minute. It may therefore use an annotated music library wherein the beats per minute of different songs are stored. In embodiments of the present invention music playback processing may be implemented in the user interface. Music playback processing may support playing of preferential music. Music playback processing may also support continuously scaling to the runner's steps per minute. This can be done instantaneously by stretching the audio, for example +/−4% of the song that is playing. When for example more than 4% of a predefined time is exceeded, e.g. 8 s, the music playback processing may switch to a different song of which the beats per minute are closer to the actual steps per minute.

Figure 6:
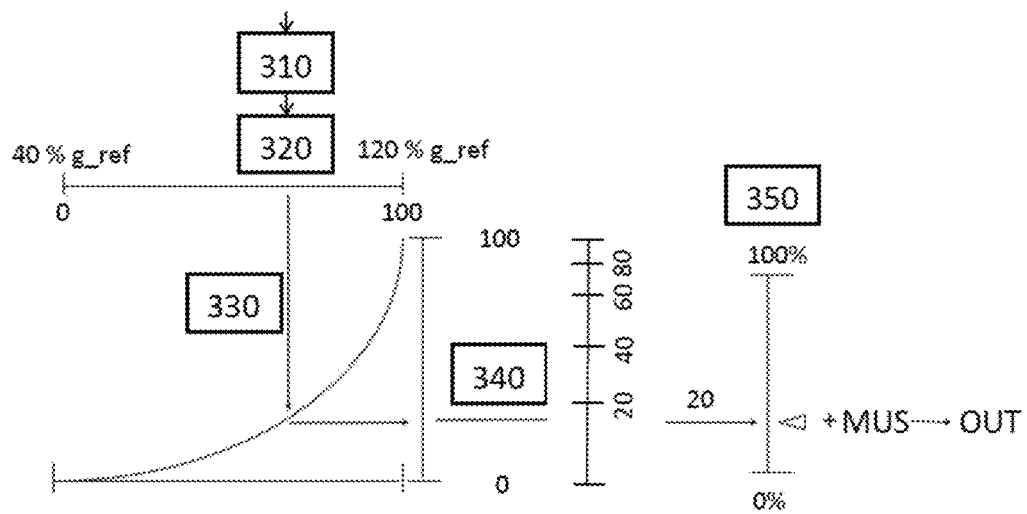
FIG. 6 shows an example of how the measure of the impact intensity can be mapped on discrete distortion levels according to embodiments of the present invention.

FIG. 6 shows an example of how the measure of the impact intensity is mapped on discrete distortion levels. In this example the empirical perception curve, output=f.a*exp(f.b.*input), as disclosed above is used. A reference measurement without music is done to obtain a reference measure of the impact intensity g_ref. From this reference measure a target value and a reference value of the impact intensity is determined. In this example the minimum value is 40% of g_ref and is normalized to zero, and the maximum value is 120% of g_ref and is normalized to 100. The block 310 in this example represents a 5-points moving average. Its input is a measured g value. Its output is scaled 320 between 0% and 100% according to the g_ref scaling. Next it is mapped 330 using the empirical perception curve. Next it is discretized. After scaling and discretization 340 the output volume of the distortion is determined based on the obtained discrete values. A pink noise volume slider 350 allows to adjust the volume of the distortion between 0% and 100%. Next the music (MUS) is added to obtain the audio output (OUT).

When for example running at the baseline g_ref the mapping may be done as follows:
100% of g_ref becomes 80 on 100 after scaling. At discretization the baseline value corresponds with the second highest noise category
120% of g_ref becomes 100 on 100 after scaling.

The outputs of the empirical perception curve are also mapped on a value between 0 and 100. In this example the distortion levels are selected in steps of 20% wherein 0% is applied when the target value of the impact intensity is reached and wherein 100% of the music volume is applied as distortion level when the maximum impact intensity is reached. The distortion is added to the music and used as an audio feedback signal to the runner.

The desired reduction can be chosen by the gait retraining expert and/or individually by the runner himself (e.g. a reduction of −30%, −50%, or any other discrete step size). By collecting tibial impact shock magnitudes of over a plurality of runners (e.g. 100 or more), it is possible to estimate magnitudes of excessive impact shock. This may be used for embedding a realistic level of impact shock reduction.

In embodiments of the present invention the running cadence is mapped to the distortion level played on top of the music. The required tempo adjustment for the song may be calculated by checking the ratio of the instantaneous steps per minute with the beats per minute of the music. If during a predetermined period of time the ratio falls outside predetermined boundaries a new song is selected.

The biofeedback system may for example comprise or have access to a database of music of different genres or of a preferred genre (e.g. pop, rock, dance, swing, world, . . . ). The music pieces may be pre-selected with a relatively constant beat and correct tempo range (e.g. between 140 and 190 bpm).

As the interface unit is adapted for providing feedback to the runner on the measure of the impact intensity of the external tibial shocks, and possibly also on the running cadence, no extra instructions on the movement adaptation of for example a trainer are required. The feedback reward consists in minimization of noise, i.e. improvement of the music quality.

The biofeedback system may be adapted for automatic calculation of a baseline steps per minute (SPM) during warm-up without any biofeedback. A target value may be determined starting from this baseline SPM. The baseline may be further tuned according to the achievable reduction after a single retraining session.

In embodiments of the present invention the steps per minute may be determined continuously during biofeedback. The steps per minute may thereby be determined on the basis of the time between two consecutive detected peaks.

The biofeedback system provides biofeedback on tibial shock using a unimodal modality and possibly also on speed to the runner when exercising, without interrupting the workout.

Methods and systems according to embodiments of the present invention may be applied to different motoric activities of repetitive genre. The use of noise provides a clear and intuitive cognitive input to the listener without the need for further explanation. Minimization of the noise provides a reward and may have positive effects on the motivation. Converting the measure of the impact intensity into distortion of music based on a predefined relationship between perceived and imposed distortion levels gives extra information to the runner which allows the runner to correctly adjust his gait.

Methods according to embodiments of the present invention may comprise providing a plurality of gait retraining sessions. Each session comprises measuring, diagnosing and providing real-time feedback during a certain period of time. In embodiments of the present invention at least for one subsequent session compared to a previous session the distortion of music for a certain measure of impact intensity has a smaller duration and/or level for the subsequent session. Thus, fading is obtained of the feedback from the previous session to the subsequent session. This faded feedback improves reinforced motor learning.

A session may for example have a duration of 20 minutes. During the first 2 sessions of running, runners may be provided biofeedback 100% of the retraining time (acquisition phase). During the last 4 sessions, feedback is faded (transfer phase) such that the runner receives less feedback during the remaining sessions. In another embodiment, the fading of the feedback may be dynamic and depends on how good the runner reacts to the biofeedback (e.g. when the PTA reduction is small in the first 3 sessions, biofeedback will play continuously).

Figure 7:
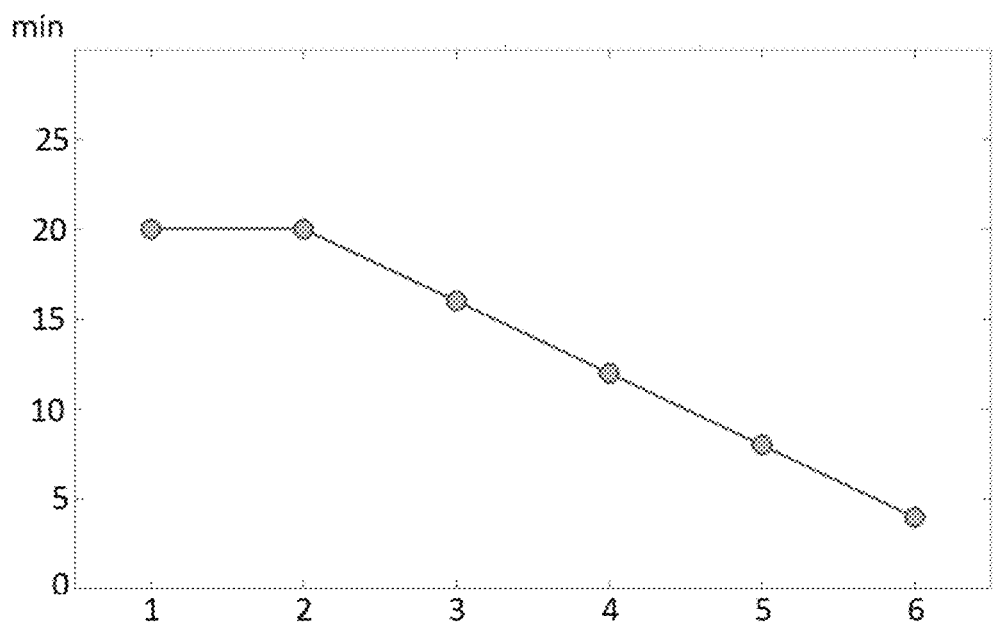
FIG. 7 shows an example of faded feedback design to reinforce motor learning in accordance with embodiments of the present invention.

An example of faded feedback design to reinforce motor learning is illustrated in FIG. 7. It shows the biofeedback time during which the distortion is applied (expressed in minutes) in function of the retraining session number.

In embodiments of the present invention the running speed counteracts tibial shock modulation due to speed alteration(s).

Figure 8:
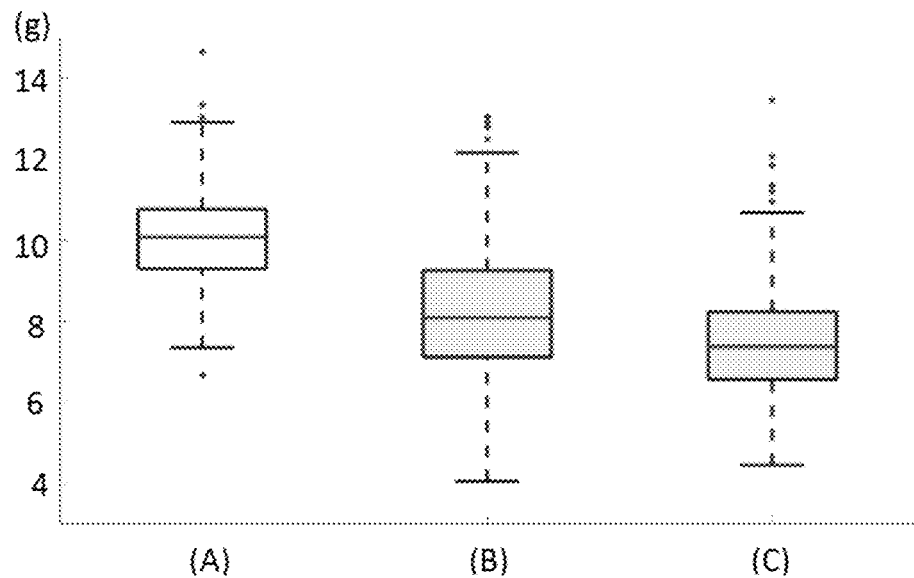
FIG. 8 shows the tibial impact shock as the peak tibial accelerations without biofeedback, and with biofeedback running conditions in accordance with embodiments of the present invention.

FIG. 8 shows a Box-and-Whisker plot showing the distribution of peak tibial accelerations (in g) experienced by a representative runner during over-ground running sessions. The PTAs are shown after running without biofeedback (A), and with biofeedback (B, C) according to embodiments of the present invention. The PTAs are shown after 10 minutes of biofeedback (0-10 minutes, B) and after 20 minutes (10-20 minutes, C) of biofeedback. Running speeds during the no biofeedback and biofeedback conditions were respectively 3.2±0.1 and 3.1±0.1 m/s (p=0.416, z=−0.813), and thus speed had no confounding effect on PTA. One retraining session with real-time biofeedback was enough to temporary decrease PTA in an over-ground setting. This is also illustrated by the table below. This table shows a comparison of the peak tibial acceleration (g) for the no biofeedback and the biofeedback (2nd 10 min.) conditions. The mean number of steps analyzed per runner are: 383 in case of no biofeedback and 872 in case of biofeedback.

|  | No biofeedback | Biofeedback |
|---|---|---|
| Mean | 10.4 | 7.7 |
| Std. Deviation | 1.5 | 0.8 |
| Minimum | 8.8 | 6.5 |
| Maximum | 12.6 | 8.5 |
| p-value | 0.043 |  |
| z-value | −2.023 |  |

All runners could decrease tibial impact shock while listening to real-time biofeedback, and this without any instruction on gait modification but simply by means of impact sonification. The reduction of −2.7 g or −26% in PTA was more than the achieved reduction in other single retraining sessions by auditory biofeedback on treadmill.

In embodiments of the present invention diagnosing the acceleration data comprises applying a peak detection algorithm for obtaining the measure of the impact intensity.

An exemplary peak detection algorithm is elaborated in the paragraphs below. The invention is, however, not limited to this algorithm.

The exemplary peak detection algorithm comprises the following steps which are successively followed at each time instance t:

1. For a new acceleration measurement at time t, in this example done with a tri-axial accelerometer (1000 Hz), a specific 1-D component of the acceleration is used to determine the measure of the impact or the standard of acceleration is calculated and used to determine the measure of the impact. This choice may be preset.
2. If the obtained value exceeds a threshold C, this value is stored as a maximum with value M'. Also, the time t' of the event of the maximum is stored. The threshold C is preconfigurable. Initially M' is assigned the threshold C and t' is assigned the value −D, wherein D corresponds with a time interval.
3. If, at time t the time of occurrence t' of the maximal value M' is smaller than t-D and the value of M' is bigger than C, then M' at time t' is registered as peak value. The obtained peak value is the measure of the impact intensity of the at least one external tibial shock. Thereafter the value of t' is set equal to t and the value of M' is set equal to C. The value of the time interval T is preconfigurable.

The parameters C and D can be optimized in function of a database of acceleration data comprising a plurality of running sessions at a constant speed. The constant speed may for example be a speed of 3.2 m/s (e.g. +/−0.3 m/s). Too low values of C and D will result in too many false positives, whereas reducing C and D will result in an increased number of false negatives. C and D may be determined in function of the speed, the impact intensity of the tibial shocks, and the step frequency. The optimal settings of C and D are also interrelated. In an exemplary embodiment of the present invention C and D are set to the following values: C=4 (g) and D=375 (ms).

Based on a more limited set of a running database at 2.55 m/s and 5.1 m/s extrapolations can be made of the set parameters to parameters for other speeds.

In embodiments of the present invention the algorithm described above may be extended with additional features. The time interval D may for example be dynamically adjusted in function of a measured step period S and possibly also other parameters such as ΔS and the threshold C. The time interval D may thereby increase with an increasing step period S and decrease with a decreasing step period S. The increase/decrease depends on the in the database observed increments and decrements for a certain step frequency. D is increased as much as possible, but small enough to avoid that two peaks are detected within the same interval when increasing the step frequency.

For example, if for a step period S of 750 ms the next step period is in 99.5% of the cases higher that 600 ms then it is possible to use a time interval D of 600 ms. For safety reasons this time interval D may be reduced by multiplying it with a factor smaller than 1. This factor may for example be dependent on ΔS.

Peak detection algorithms wherein the parameters are dynamically adjusted may also comprise an initialization module for re-initializing the parameters to default values in case of inconsistencies (e.g. when no peaks are detected at expected moments in time).

The threshold C may be adjusted to the baseline level of the impact peaks (the default value may for example be 4 (g)). For high impact runners C can be increased in order to lower the risk of false positives in the swing phase. If runners start decreasing their impact intensity the threshold can be decreased dynamically or vice versa. The measure of the decrement or increment may be determined from the observed variation in the peak height in successive steps and from the observed height of the acceleration signal in the swing phase. The higher the threshold value C can be set, the more false positives are prevented (which is preferable over preventing false negatives) and the faster the algorithm (providing setting the threshold itself is not too complex).

The determined peaks are a measure of the impact intensity and are used for sonification of the impact. The peak detection algorithm may be combined with the goals for impact reduction. Peaks for which sonification is not required should not be detected. In the sonification algorithm, the distortion may be gradually reduced when no peaks are detected. This can for example be achieved by multiplying the noise level with a factor smaller than one (watermark), when a period of time is passed which is larger than the previous step period and during which no peak detection occurred. This way the threshold C can be set high for high impact runners.

In embodiments of the present invention the peak detection algorithm may search in a time interval which is determined in function of the expected step period. A high value will only be recognized as a peak if it occurs within the expected time interval. The size of the expected time interval may be determined based on the step frequency and may be dynamically adjusted. Based on statistical analysis on the database the deviation between successive step periods may be determined. These deviations may be determined for a specific step frequency.

An exemplary peak detection algorithm may further comprise the following steps:

A boolean isRunning indicates which branch of the algorithm is traversed. Initially this boolean is set to false.

If isRunning=false. The algorithm is traversed as described before. As from the moment two peaks are determined the step period S is determined as the step period between the peaks. From the moment three step period are registered (in this algorithm only the last three step periods are memorized) the algorithm determines whether the differences between them are acceptable for a stable pattern and reliable measurement results. If the differences between the three time periods are acceptable, S' is set equal to the average of the time periods. isRunning is set equal to true.

If isRunning=true.

The window wherein the peaks are searched is [t'+S'−a, t'+S'+b] with a,b dynamic parameters (which may have the following starting values a=375 en b=375), t' is the moment in time of the previous peak and S' is the averaged step period. If the moment in time t is within the window, the value of a component or the value of the norm is used to determine a maximum value M, as was discussed before.

If t=t'+S'+b, then M is selected as potential peak value.

The step period S is determined, and it is verified whether it approaches the averaged step period S' sufficiently.

If the step period S is within an acceptable range from the averaged step period S', then M is determined as peak (t'=t) and the new averaged step period is determined (e.g. S'=[3×S'+2×S]/5]).

The parameters a=f(S') en b=g(S') with f and g functions of the step period are calculated. This can for example be according to the following formulas: a=0.4×S' and b=0.4×S'. The functions f and g possibly may be more complex and may depend on other parameters (e.g. ΔS', C). See also the previous extension.

The averaged peak height M' is calculated (e.g. M'=[3×S'+2×M]/5])). The new value of C is calculated C=h(C, S', M, ΔS, ΔM) with h possibly a function of C, S', M', ΔS, ΔM, . . . .

The algorithm waits until t=t'+S'−a.

If the step period S is not within an acceptable range from the averaged step period S', a counter is incremented. The averaged step period S' remains. Only if the counter has reached a certain value new initial values are determined with isRunning=false.

Experimental results of a method in accordance with embodiments of the present invention are discussed in the following paragraphs. From these results it can be concluded that over-ground retraining, using a method in accordance with embodiments of the present invention, is effective for tibial shock reduction. Ten runners with high tibial shock (11.1±1.8 g) ran for a total of 20 minutes at ~3.2 m·s$^{-1}$ on a tartan track while actively listening to music-based feedback on their shock level in real-time, in accordance with embodiments of the present invention. The music was synchronized to step frequency and distorted according to the momentary shock level. An over-ground retraining session with real-time biofeedback was enough to decrease the tibial shock by 3 g or 27% (p=0.001, Wilcoxon signed-rank), and this without guided instructions on gait modification. Furthermore, the running speed remained stable, having no confounding effect on the shock magnitude. The running cadence did not substantially increase on group level within a session, suggesting personalized kinematic responses for lower impact running. These findings show the potential of wearable biofeedback systems, according to embodiments of the present invention, that eliminate the need of exclusive retraining in laboratory and clinic settings, allowing to retrain runners in more natural environments.

When running, a footfall may give rise to a shock that reaches several times the gravitational constant (g) during sub-maximal, over-ground running. In the experiments below this shock is measured unidirectionally at tibial level as the axial peak tibial acceleration (APTA).

Figure 9A:
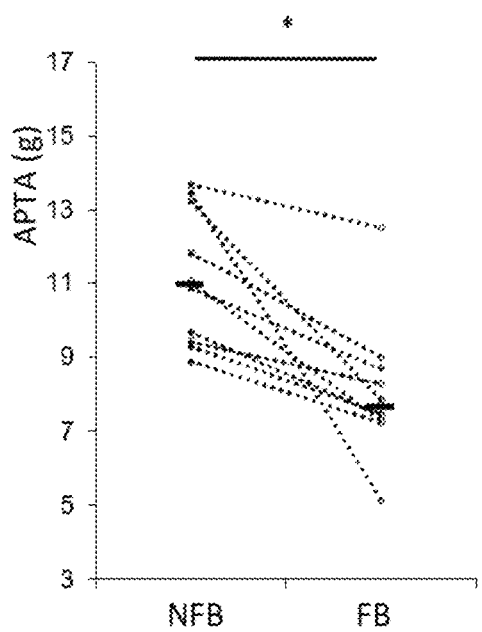
FIGS. 9(a) and 9(b) show experimental results obtained from runners which are running with and without a biofeedback system in accordance with embodiments of the present invention.
Figure 9B:
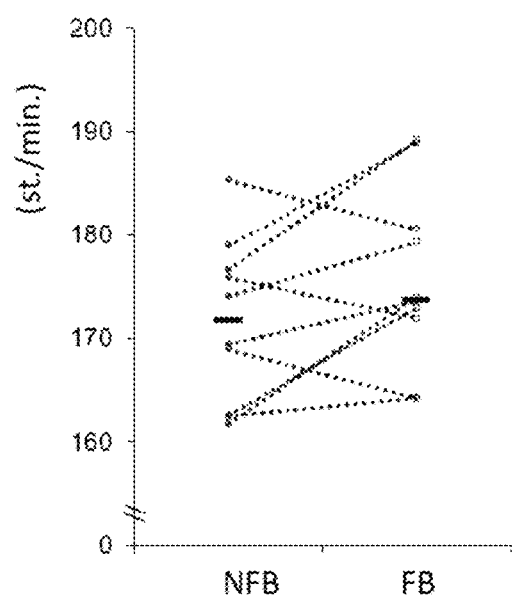

The graphs of FIG. 9 show the obtained experimental results. FIG. 9(*a*) shows for each runner the APTA (in g) and FIG. 9(*b*) shows for each runner the running cadence (in steps per minute). In both graphs one set of data is obtained when running without biofeedback system (NFB data) and another set of data is obtained when running using a biofeedback system (FB data) in accordance with embodiments of the present invention. The data for each runner are represented by the circles. The short horizontal lines indicate the median level of the variable of interest within a condition, wherein a first condition corresponds with running without biofeedback system and a second condition corresponds with running using a biofeedback system. The mark "*" indicates p<0.05.

During the no-biofeedback period, the analyzed APTA was 11.1±1.8 g, ranging from 8.9 to 13.6 g between-participants. The participants were able to reduce APTA by 27% to 8.1±1.9 g (p=0.001, mean negative rank=5.50, z=−2.81) by means of the music-based real-time biofeedback (FIG. 9(*a*)), and this without guided instruction on gait modification.

Figure 10:
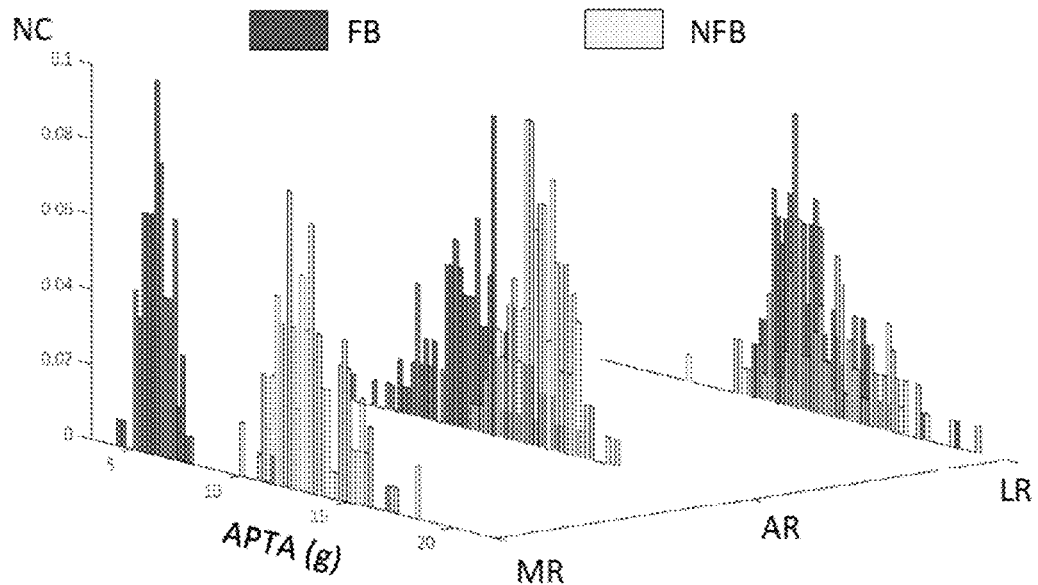
FIG. 10 shows the APTA's distribution for an average, most pronounced, and least pronounced responder, obtained using an experiment with no-biofeedback and with biofeedback in accordance with embodiments of the present invention.

FIG. 10 shows the APTA's distribution for the average (AR), most (MR) and least (LR) pronounced responder during the no-biofeedback and during the biofeedback conditions in accordance with embodiments of the present invention. The footfalls of each responder have been normalized to the number of footfalls of that participant counted in both conditions (normalized count NC). While most shocks decreased in magnitude, few footfalls have an APTA that would still be categorized as high for these three runners.

During the biofeedback run, the momentary ratio of the runner's tempo and music tempo (SPM/BPM) was 1.00±0.03. The music's beats per minute was continuously aligned to the tempo of the runner's steps per minute.

Figure 11:
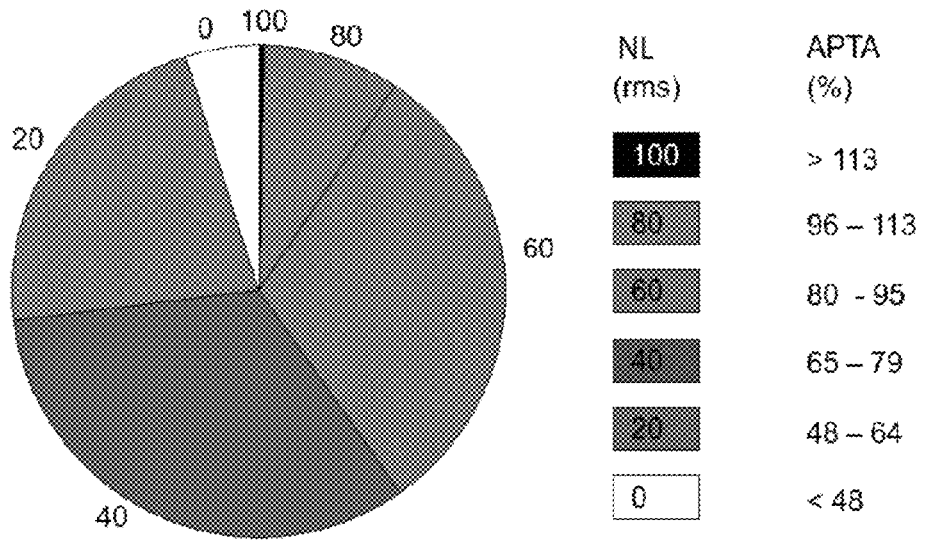
FIG. 11 shows different noise levels for different levels of tibial shock applied during an experimental run with biofeedback in accordance with embodiments of the present invention.

In this experiment the level of noise loudness added to the synchronized music varied from maximum to zero, on group level. The mapping used in this experiment is shown in FIG. 11 which shows the proportion of the pink noise generated during the 20 minutes biofeedback run for the group of runners. Level 0 represents the 'music only' category without superimposed noise. The level of noise loudness added to the synchronized music has been subdivided into 5 categories. Each level of noise loudness (NL) corresponds to a level of tibial shock relative to the runner's baseline g-value. In the experiment the runners could at least partly remove the superimposed noise by adjusting their gait.

Running speeds during the no-biofeedback and biofeedback conditions were respectively 3.15±0.12 and 3.13±0.15 m·s$^{-1}$ (p=0.520, z=−0.71). The running speed for the laps chosen for APTA comparison did also not differ (p=0.090, z=−1.72) and also remained within the a priori permitted boundary of ±0.20 m·s$^{-1}$. Consequently, speed had no confounding effect on the proportion of generated noise loudness nor on the pre-post differences in APTA. The group's steps per minute tended to increase (p=0.053, z=−1.682, positive mean rank=+6.3).

The mean session rating of perceived exertion was 4 (somewhat hard) with individual values ranging from 2 to 9. In this group of retrainers, the participant reporting the highest rating of perceived exertion also reported the lowest combined training volume and training speed. The perceived exertion did not correlate to the absolute (p=0.530, r=−0.29) nor relative (p=0.618, r=−0.23) decreases in APTA, implying that the attained level of exertion did not seem to influence the reduction in tibial shock achieved by these runners.

The invention claimed is:

1. A method for gait retraining of a runner, the method comprising
   measuring acceleration data of at least one lower leg of the runner using a sensor which is adapted for monitoring external impact shocks;
   diagnosing the acceleration data using a processing unit, thereby determining a measure of the impact intensity of at least one external tibial shock;
   and providing real-time feedback to the runner using an interface unit by converting the measure of the impact intensity into distortion of music to a level which is perceived by the runner as a measure for the impact intensity whereby, for the distortion, a sound type is continuously added to the music,
   wherein the conversion is done based on a predefined relationship between perceived distortion levels and imposed distortion levels,
   wherein the sound type is pink noise,
   wherein the predefined relationship is an exponential fit, and
   wherein the runner aims to reduce the distortion of the music by adjusting his or her gait.

2. The method according to claim 1, the method comprising measuring the running speed and providing real-time feedback to the user about the running speed.

3. The method according to claim 1, wherein the real-time feedback is only provided if the measure of the impact intensity is crossing a predefined threshold.

4. The method according to claim 1, wherein distortion of music is achieved by adding white noise, or by adding pink noise, or by adding amplitude modulated noise to the music, or by downsampling the music, or by decreasing the volume of the music.

5. The method according to claim 1, wherein the distortion of music is changed in steps of discrete pre-defined levels.

6. The method according to claim 1, the method moreover comprising adjusting a tempo of the music to the tempo of the running cadence.

7. The method according to claim 1, the method comprising providing a plurality of gait retraining sessions wherein each session comprises the measuring, diagnosing and providing real-time feedback during a certain period of time and
   wherein at least for one subsequent session compared to a previous session the distortion of music for a certain measure of impact intensity has a smaller duration and/or level for the subsequent session, thus obtaining fading of the feedback from the previous session to the subsequent session.

8. The method according to claim 1, wherein diagnosing the acceleration data comprises applying a peak detection algorithm for obtaining the measure of the impact intensity.

9. The method according to claim 8, wherein the peak detection algorithm comprises determining a maximum value of the acceleration data within the first 50 ms after foot contact.

10. The method according to claim 8, wherein the peak detection algorithm comprises determining a size of a 1D-component of the acceleration data for obtaining the measure of the impact intensity.

11. The method according to claim 10, wherein the peak detection algorithm comprises finding a peak of which the size of the 1D component is larger than a peak detection threshold (C), and finding this peak within an expected time window wherein the size (D) of the time window is dependent on the expected pace period.

12. A biofeedback system for gait retraining of a runner, the biofeedback system comprising:
- at least one sensor mountable against the lower leg of the runner and adapted to measure acceleration data along at least one axis,
- a processing unit adapted for diagnosing the acceleration data thereby determining a measure of the impact intensity of at least one external tibial shock,
- an interface unit adapted for providing real-time feedback to the runner by converting the measure of the impact intensity into distortion of music to a level which is perceived by the runner as a measure for the impact intensity whereby, for the distortion, a sound type is continuously added to the music,
- wherein the conversion is done based on a predefined relationship between perceived distortion levels and imposed distortion levels,
- wherein the sound type is pink noise,
- wherein the predefined relationship is an exponential fit, and
- wherein the runner aims to reduce the distortion of the music by adjusting his or her gait.

13. The biofeedback system according to claim 12, wherein the biofeedback system moreover comprises a speed sensor, or is adapted for interfacing with a speed sensor for measuring a speed of the runner and
- wherein the processing unit is adapted for diagnosing the acceleration data in function of the measured speed and/or wherein the interface unit is adapted for providing real-time feedback of the measured speed.

14. The biofeedback system according to claim 12, wherein the biofeedback system is adapted for storing the measured acceleration data and/or the measures of the impact intensity and/or the measured speed.

15. The biofeedback system according to claim 12, the biofeedback system moreover comprising a communication unit adapted to synchronize data with at least one external measurement system.

* * * * *